United States Patent [19]

Molin et al.

[11] Patent Number: 4,760,022

[45] Date of Patent: Jul. 26, 1988

[54] STABILIZED PLASMIDS

[75] Inventors: Søren Molin, Holte; Kenn A. Gerdes, Virum, both of Denmark

[73] Assignee: A/S Alfred Benzon, Copenhagen V, Denmark

[21] Appl. No.: 610,985

[22] PCT Filed: Sep. 15, 1983

[86] PCT No.: PCT/DK83/00086

§ 371 Date: May 15, 1984

§ 102(e) Date: May 15, 1984

[87] PCT Pub. No.: WO84/01172

PCT Pub. Date: Mar. 29, 1984

[51] Int. Cl.$^4$ .................. C12P 21/00; C12P 19/34; C12N 15/00; C12N 1/20

[52] U.S. Cl. .................. 435/320; 435/70; 435/91; 435/172.3; 435/253; 435/68; 935/29; 935/38; 935/56

[58] Field of Search .................. 435/172.3, 317, 91, 435/240; 935/38, 56, 60, 24, 29; 436/253, 70

[56] References Cited

U.S. PATENT DOCUMENTS 4,487,835 12/1984 Uhlin et al. .................. 435/317

OTHER PUBLICATIONS

Nordstrom et al. (1980) Plasmid, vol. 4, pp. 332–339.
Nordstrom, K. et al. (1980) Plasmid 4:215.
Meacock, P. et al. (1980) Cell 20:529.
Remant, et al. (1981) Gene 15:81.
Miki, T. et al., Jan. 1980, J. Bacteriol. 141:87.
Gerdes, K. et al., Jan. q985, J. Bacteriol, 161:292.
P. Gustafsson in New Hosts and Vectors for Recombinant DNA, Technology, IVA-PM No. 3, Mar. 1982, pp. 75–83.
R. W. Seelke et al., Plasmid 7, 163–179 (1982).

Primary Examiner—Thomas G. Wiseman
Assistant Examiner—Stephanie Seidman
Attorney, Agent, or Firm—Stiefel, Gross & Kurland

[57] ABSTRACT

Plasmids which are in themselves unstably inherited or which have become unstable due to the insertion of a DNA fragment comprising one or more genes not naturally related to the plasmid are stablized by means of a partitioning function exerted by a par region, especially a plasmid R1 par region, inserted into the plasmid on a DNA fragment which may be the length of the wild-type R1 EcoR1-. A fragment, but which is preferably shorter than this fragment, and which may comprise the R1 par region A, the R1 par region B or both these R1 par regions. The stabilization obtained for several different types of plasmid, especially by employing both R1 par regions, approaches the stability level of wild-type plasmids, i.e. they typically have a frequency of loss of less than $5 \times 10^{31}$ $^6$ per cell per generation. Such stabilized plasmids are useful in large-scale production of gene products as no particular bacterial strains or mutants are needed to secure plasmid maintenance, and as is not necessary to employ a specific composition of the nutrient medium in which the host cells are grown in order to prevent loss of the plasmid from the bacterial population.

27 Claims, 5 Drawing Sheets

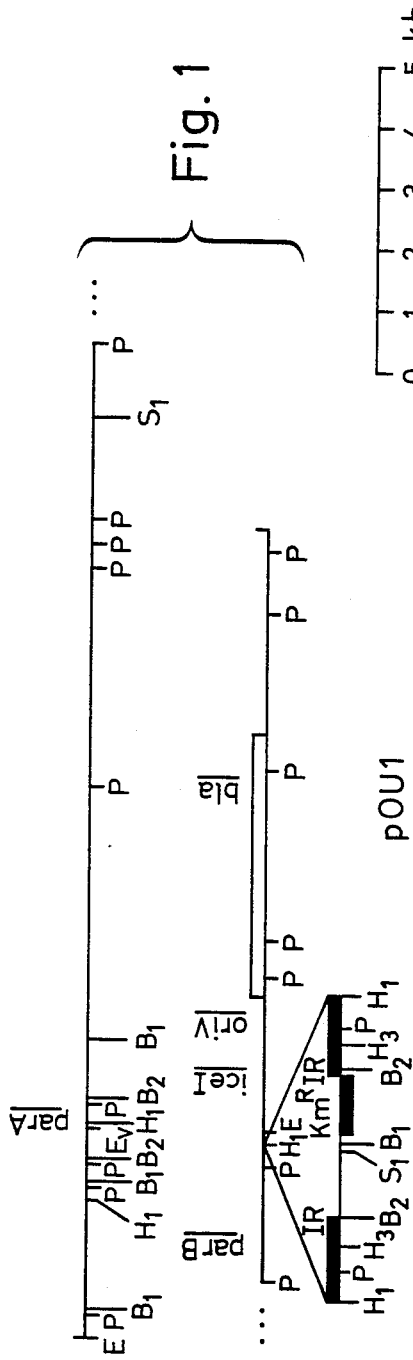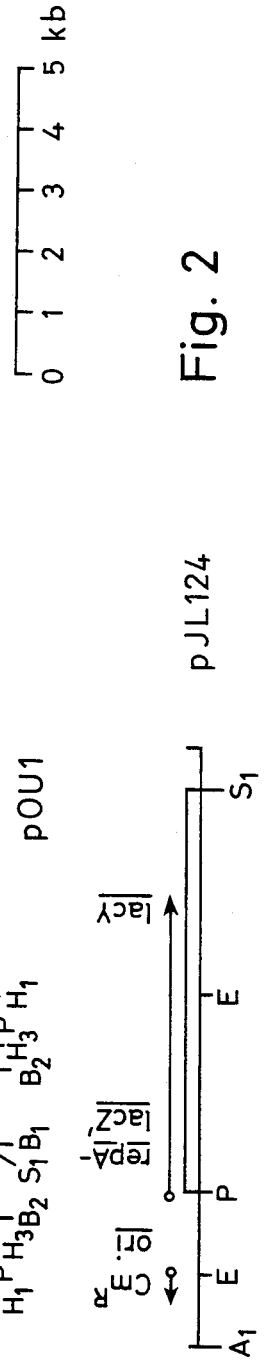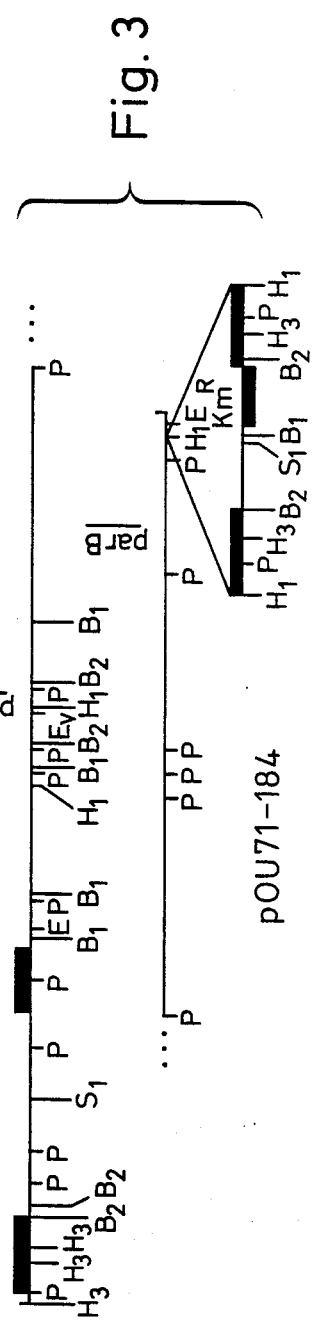

STABILIZED PLASMIDS

The present invention relates to the stabilization of plasmids useful in the field of recombinant DNA technology for production of genes and their products.

TECHNICAL BACKGROUND

The continued maintenance of most natural plasmids, even in the absence of selection pressure (factor which secure the growth of only those ogranisms which harbour the plasmids; an example is an antibiotic in the nutrient medium in the case of a plasmid carrying a gene mediating resistance to the antibiotic), suggests that plasmid maintenance functions have been evolved to secure the continued presence of these extrachromosomal elements with high efficiency. The plasmid maintenance functions primarily consist of the replication genes including their control circuits which regulate the plasmid concentration in the cell. In growing cells the replication control system monitors the number of plasmid copies and corrects deviations from the average by increasing or decreasing the probability for plasmid replication. However, no replication control system can prevent the occurrence of cells with very few or just one copy of the plasmid, and from such cells the possibility of formation of a plasmid-free daughter cell is obvious. This problem is of course greatest for low copy number plasmids. Moreover, a passive distribution of plasmid molecules at cell division will inevitably result in a certain frequency of plasmid-free cells. Since the loss of a plasmid molecule from a cell is irreversible, the consequences of such an unstable situation will be that the entire population eventually becomes plasmid-free.

Besides a random distribution of plasmids at cell division, other factors may influence the rate of loss of plasmids from a culture of cells grown in the absence of selection for the maintenance of the plasmid. For example, some plasmids require a specific recombination system in order to resolve two newly replicated molecules (Austin et al., Cell 25, 1981, pp. 729–36). In the absence of resolution, multimers will form (interlocked), and in this way even a high copy number plasmid may appear as a low copy number plasmid at the level of distribution to daughter cells, since the probability of generating plasmid-free cells will increase with increasing numbers of plasmid molecules interlocked in multimeric structures. Another phenomenon which is often observed in recombinant DNA technology is the conversion of a stable cloning vector into an unstable hybrid plasmid as a result of insertion of a DNA fragment, whose presence either causes a decrease in plasmid copy number or gives rise to a detrimental product that negatively interferes with cell growth.

In all such cases, plasmid segregation and loss occurs with a frequency (high or low) which cannot easily be controlled from the outside.

The stability of natural plasmids, and especially of low copy number plasmids, suggest that, in addition to the replication control system, a second set of maintenance functions exists which actively takes part in an ordered distribution of the plasmid molecules at cell division. Such functions have been formed partitioning functions, and studies, e.g., Meacock et al., Cell 20, 1980, pp. 529–42, Nordström et al., Plasmid 4, 1980, pp. 332–49, Seelke et al., Plasmid 7, 1982, pp. 163–79, have now shown that these are at least partly encoded by the plasmids themselves (in par regions). Thus, certain plasmid deletion mutants have lost their stable maintenance or inheritance despite their normal wild-type replication behaviour, indicating that a plasmid specified function securing stability has been removed. (c.f. Nordström et al., op.cit.).

As many of the plasmids employed as vectors in recombinant DNA technology have been deleted of a large amount of DNA compared to the wild-type parent plasmid, they are susceptible to being unstably inherited. This poses a serious problem since instability of a plasmid will ultimately result in a complete loss of the plasmid from the cells, and in any case will reduce the relative yield of plasmid-encoded gene products. This problem is particularly pronounced in large-scale prodution of gene products where growth of microorganisms under selection pressure, e.g. an antibiotic, is normally not feasible and often at least undesirable from an environmental point of view, and where the microorganisms are grown for a large number of generations. Vectors which are only present in a few copies per cell are most likely to be unstably inherited and therefore lost from the cells. Even plasmids which ordinarily have a relatively high copy number securing a relative stability of the plasmid have been known to become unstable when DNA fragments carrying genes not naturally related to the plasmid are inserted therein.

DISCLOSURE OF THE INVENTION

The present invention relates to plasmids which carry an inserted gene or genes not naturally related to the plasmid and which additionally carry an inserted DNA fragment exerting a partitioning function. The term "inserted" is meant to indicate that the gene(s) or DNA fragment has been introduced into the plasmid at one stage during the construction of the final plasmid.

In the present context, the term "a partitioning function" denotes a function which ensures an ordered distribution of the plasmid molecules at cell division and which is encoded by a region of a plasmid which, dependent on the type of plasmid expressing the function, may comprise one or more genes. As mentioned above, such regions are found in naturally occuring, or wild-type, plasmids, but plasmids which express a Par+ phenotype, i.e. on which the partitioning genes are present, and which also carry an inserted gene or genes not naturally related to the plasmid are believed to be novel. In this context, plasmids are defined as naturally occurring extrachromosomal element in microorganisms, which elements it is possible to isolate as such, or derivatives thereof.

The plasmids of the invention may be used as cloning or production vectors in the field of recombinant DNA technology for the purpose of obtaining a wide variety of products for technical or medical purposes directly or indirectly mediated by the inserted gene or genes, particularly polypeptides and proteins or fragments thereof, enzymes, and a number of non-proteinaceous products or reactions of enzymes, low molecular weight products such as hormones, and nucleic acids; products of eukaryotic, especially mammalian, genes are of particular interest.

In accordance with a preferred embodiment of the present invention, the partitioning function is one which, in nature, is expressed by a region of the wild-type resistace plasmid R1, and therefore in the following referred to as an R1 par region. According to the present invention, such a region has been found to cause partial or full stability of not only unstable R1 miniplasmids carrying a gene or genes not naturally related to the plasmid, but also of frequently segregating plasmids not related to plasmid R1 carrying a gene or genes not naturally related to the plasmid. Another example of a particularly valuable partitioning function is that found on the wildtype plasmid F (Seelke et al., op.cit.) which also confers a high degree of stability to the recipient plasmid. In the following, reference will primarily be made to the R1 Par function, although it should be understood that many of the phenomena associated with the R1 Par function will also apply to other Par functions and that the general concept of the invention in its broad scope is not limited to the R1 Par function.

It has previously been indicated that the partitioning function of plasmid R1 is exerted by the so-called EcoR1-A fragment (cf. Nordström et al., Plasmid 4, 1980, pp. 332–49). In the course of research leading to the present invention, it has surprisingly been found that the EcoR1-A fragment which has a length of about 19 kb (19,000 base pairs) comprises two and only two distinct regions conferring a Par+ phenotype on the recipient plasmid. These regions are situated at either end of the EcoR1-A fragment and no other DNA sequence in the EcoR1-A fragment is at present believed to have any plasmid stabilizing function. For the present purposes, the two regions have been designated the par region A and the par region B, respectively, abbreviated as parA and parB, respectively.

As it is advantageous to operate with as small DNA fragments as possible, because small fragments are easier to insert into the plasmid and the resulting plasmids are easier to transform to host cells, one aspect of the present invention relates to plasmid which carry an inserted DNA fragment which is shorter than the EcoR1 fragment of plasmid R1 and contains an R1 par region. This inserted DNA fragment normally comprises, as its major component, the R1 par region A region, the R1 par region B region or both R1 par region A and R1 par region B. This means that substantially all of the DNA fragment inserted into the hose plasmid is constituted by either or both of the par regions, and the remainder of the DNA on the fragments is present primarily to provide suitable restriction sites, providing the DNA fragments with the desired ends which are easily compatible with a corresponding or compatible restriction site on the recipient plasmid. Such ends may also be provided by means of linkers. It is, however, important to bear in mind that the DNA fragment comprising the par region A and the DNA fragment comprising the par region B may be introduced separately and sequentially into the same plasmid which will then be phenotypically identical with a plasmid in which the phenotype ParA+, ParB+ has been established by inserting the par region A and par region B on the same DNA fragment. For instance, if it is desired to further stabilize a plasmid already carrying a par region, such as the parB region, the plasmid may be restricted with an appropriate restriction enzyme and a DNA fragment having ends which are compatible with this restriction site and carrying the other par region, such as the parA region, may then be inserted. The opposite procedure, i.e. insertion, in a similar manner, of a parB region on a plasmid already carrying a parA region, may also be employed.

In accordance with this, interesting plasmids are plasmids in which the inserted DNA fragment comprising R1 par region A and R1 par region B has a length not exceeding about 6 kb, especially not exceeding about 4 kb, in particular not exceeding 3 kb. When the inserted DNA fragment includes the R1 par region A, it will normally have a length not exceeding about 4 kb, especially not exceeding about 2.5 kb, in particular not exceeding about 2 kb. When the inserted DNA fragment comprises the R1 par region B, it will normally have a length not exceeding about 2 kb, especially not exceeding about 1.5 kb, in particular not exceeding about 1 kb. The preference for small DNA fragments for the reasons stated above should not, however, exclude the possibility of obtaining plasmid stability by inserting the entire EcoR1-A fragment; this may for instance be acceptable where the size of the plasmid to be stabilized is less critical. If the fragment is inserted in toto, it may be advantageous for screening purposes to provide the DNA fragment with a gene mediating antibiotic resistance. If, however, for some reason, it is desired to reduce the size of the EcoR1-A fragment, this may be done in various ways, such as by partial restriction of the EcoR1-A fragment with the restriction enzyme PstI, or by excising each R1 par region from the large fragment, and transferring each region sequentially to the same DNA fragment which may then be inserted into the plasmid to be stabilized.

The plasmids which are stabilized in accordance with the principles of the invention may be either plasmids which have natural relation to the partitioning region inserted, such as R1 miniplasmids which are stabilized by means of an inserted R1 par region (R1 miniplasmids have been deleted of much of the original R1 DNA and do consequently not usually in themselves contain an R1 par region), or they may be plasmids which do not have a natural relation to the partitioning function. It is interesting to note that efficient partitioning functions useful according to the present invention are capable of securing a satisfactory stability not only of plasmids to which they are naturally related, such as in the case of the stabilization of R1 miniplasmids with an R1 par region, but also of plasmids to which the partitioning function is not naturally related. An example of the latter is the insertion of an R1 par region in a non-R1 plasmid, such as a pMB1 plasmid or a derivative thereof, such as a pBR322 plasmid or a derivative thereof (these plasmids are ordinarily stable, but are susceptible to becoming unstable when a gene or genes not naturally related to the plasmid are inserted). Another example is the use of an R1 par region for stabilizing certain plasmid types which, at least at one stage during the cultivation of bacteria harbouring the plasmid, have a low copy number, e.g. a copy number of 0.5–5 copies per cell, such as low copy number broad host range plasmids (plasmids which are able to replicate in many different host strains or species; this class includes the so-called shuttle vectors which are able to replicate in two or more types of microorganism) and derivatives thereof, e.g. RK2. Apart from R1, other plasmids of the incompatibility group IncFll requiring stabilization include, e.g., R100 and R6. The use of an R1 par region for the stabilization of unstable plasmid F derivatives also lies within the scope of the present invention.

One type of plasmids for which a stabilization in accordance with the present invention is important is conditional runaway replication plasmids, i.e. plasmids which, when host microorganisms harbouring the plasmids are grown under certain conditions, have a constant low plasmid copy number, and which, when the microorganisms harbouring the plasmid are grown under certain different conditions, lose their replication control so that the plasmid copy number increases exponentially until the host cell ceases to grow. Runaway replication plasmids for which the stabilization according to the invention is particularly vital are runaway replication plasmids with a copy number not exceeding about 3–5 copies per cell, and especially such plasmids, the copy number of which does not exceed about 0.5–1 copy per cell (the figure 0.5 is understood to mean that the frequency of replication is less than one per cell cycle) when the microorganisms harbouring the plasmids are grown under those conditions which ensure such a low plasmid copy number and which, when the host microorganisms are grown under certain differing conditions ensuring a substantially increased plasmid copy number, has a copy number in the range of at least about 500–1000 copies per cell.

The low plasmid copy number under certain conditions (typically a low temperature such as a temperature of about 30° C.) is desirable when plasmids are used as vectors for the insertion of foreign genes coding for products which are partially toxic or lethal to the host cell, as due to the low replication rate of the plasmid at, e.g., a low temperature, the genes are only expressed in small amounts, if at all, so that the cells remain undamaged in the propagation stage of the culture. However, in plasmids with such an extremely low copy number as that stated above under propagation stage conditions, such as growing cells at a low temperature, the lack of a par region results in loss of a plasmid from the microbial population with a frequency of about 1% per generation for plasmids with a copy number not exceeding 3–5 copies per cell when these are grown under the conditions securing such a low copy number. The frequency of loss for plasmids with a copy number not exceeding about 0.5–1 copy per cell is about 5%/cell/generation. It is obvious that without any partitioning function to stabilize them, the plasmids would be lost from the cells before the cells had reached such a density in the nutrient medium that it would be economic to induce runaway replication; this is particularly the case in large-scale production requiring many hundreds of generations of cell growth to reach production size culture.

Such runaway replication may be made conditional by inserting a regulatable promoter upstream of the native replication control gene(s) of the plasmid (a detailed description of this phenomenon is found in Applicant's co-pending application entitled "Plasmids with Conditional Uncontrolled Replication Behaviour" and filed on the same day as the present application). Plasmids which have a runaway replication behaviour may be of many different types, but preferred runaway replication plasmids are R1-type plasmids.

In the present specification, the term "stability" (and related terms) is intended to mean a frequency of loss of the plasmid from the hose cell of less than $2 \times 10^{-4}$ per cell per generation. In fact, it is possible to obtain plasmids which are as stable as wild-type plasmids, i.e. with a frequency of loss of less than $3 \times 10^{-6}$ per cell per generation, which corresponds to the level of mutation rate of genes, by incorporating a Par function in the plasmid. This latter frequency of loss (LF) value is evident when plasmids are stabilized by both R1 par region A and R1 par region B, such as when the entire EcoR1-A fragment has been inserted in the plasmids.

As mentioned above, the Par+ phenotype of plasmid R1, however, has been localized to each separate par region on the EcoR1-A fragment. It has been found that each of these par regions exert a stabilizing effect on unstable plasmids, which may be defined as plasmids lacking a stabilizing, or partitioning, function. Such plasmids which phenotypically are Par− are usually lost from the host cell with higher or lower frequency; thus, for instance plasmid R1 derivatives deleted of the par region are lost from the host cell with a frequency of about $1.5 \times 10^{-2}$ per cell per generation. Similarly, plasmid p15 derivatives, which are Par− are lost with a frequency of about $1 \times 10^{-2}$/cell/generation, and some plasmid pMB1 (pBR322) derivatives (such as the one described in Example 3.3) may be lost with a frequency of about $6 \times 10^{-3}$/cell/generation. Conversely, R1 plasmids stabilized with either parA or parB alone have an LF value of about $10^{-4}$ per cell per generation, corresponding to a 100-fold stabilization when a DNA fragment carrying either of these par regions is inserted into an unstable vector; the figures for a corresponding p15 derivative are about $8 \times 10^{-4}$ (Par A+), $1 \times 10^{-6}$ (Par B+), and the figures for a corresponding pMB1 derivative are $5 \times 10^{-5}$ (Par B+). Plasmids which carry both the par A and the par B region have an LF value of approximately $10^{-6}$ per cell per generation, or a $10^4$-fold stabilization. For easy reference, the results for stabilized and unstable replicons of different origins are shown in table 1. This indicates that each par region acts independently of the other, that the par regions are approximately equally efficient in stabilizing at least R1 and p15 plasmids and that their action or effect is cumulative. This finding may be utilized when determining the degree to which an unstable plasmid need be stabilized. If a less drastic stabiliztion is required, i.e. if it is estimated that the plasmid to be stabilized is not excessively unstable (with an LF value of less than $10^{-2}$/cell/generation), it may be sufficient to insert a DNA fragment containing one of the par regions in order to obtain a satisfactory stability, i.e. prevent a gradual loss of the plasmid from a large-scale production population of bacteria over several hundred generations. On the other hand, if the plasmid is very unstable, (width an LF value of more than $10^{-2}$) it may be necessary or at least advantageous to insert both par regions in order to secure extremely stability of the plasmids.

TABLE 1

| Frequencies of loss/cell/generaton of different replicons | | | | |
|---|---|---|---|---|
| | Frequencies of loss $\times 10^{-4}$/cell/generaton | | | |
| Type of | Par Phenotype | | | |
| Replicon | Par− | ParA+ | ParB+ | ParA+ ParB+ |
| R1 | 150 | 0.6 | 1.0 | 0.04 |
| p15 | 100 | 8.0 | 0.01 | 0.01 |
| pMB1 (pBR322) | 60 | ND[1] | 0.5 | 0.1 |

[1]ND = no data

These measurable LF values may be utilized when plasmids of any of the types defined above are to be used as vectors in the production of gene products, and should thus contain at least one gene not naturally related to the plasmid. A further aspect of the present invention thus relates to a method of producing a gene product from plasmid DNA in which bacteria harbouring a par-stabilized plasmid with any of the above-described characteristics are cultivated and the gene product of the plasmid is harvested from the bacterial culture. The cultivation per se is suitably performed using conventional techniques including conventional nutrient media which are known to be optimal to the bacterial species in question. It is worth noting that due to the stabilization, a specific composition of the nutrient medium is not needed. Also, the harvesting of the gene product is performed in accordance with well-known methods adapted to the identity and properties of particular gene product prepared, the properties of the host bacterium, etc. The cultivation is continued for at least 100 generations of the bacteria; in large-scale production, the number of cell generations needed to propagate the bacteria may exceed 100 generations. Under these circumstances, the LF value of the plasmid will be so selected by the presence of a par region therein that the loss of the plasmid is less than $2 \times 10^{-4}$/cell/generation. This LF value will usually be attainable by means of one par region alone. In some cases it is, however, preferred to obtain LF values for the plasmid of less than $10^{-5}$/cell/generation, in particular less than $5 \times 10^{-6}$/cell/generation.

Although these very low LF values may in some instances be attainable by the insertion of only one par region (particularly R1 par region B), they will usually need the presence of both R1 par regions.

A further aspect of the invention relates to bacteria harbouring plasmids of the above-defined type. It is a particular advantage of the plasmids of the invention that no particular mutants or strains are needed to secure plasmid maintenance. Thus, any species and strain of bacterium capable of harbouring such plasmid may be employed, such as gram-negative bacteria. A specific example of a bacterium in which plasmids according to the present invention are able to replicate and maintain their stability is *Escherichia coli*.

Finally, the present invention relates to a DNA fragment which comprises, as its major component, an R1 par region. This implies that substantially all of the DNA fragment inserted into the host plasmid is constituted by either of both of the par regions, and the remainder of the DNA is present to provide suitable restriction sites for insertion with a compatible restriction site on the recipient plasmid. The inserted DNA fragment comprising R1 par region A and R1 par region B should, in accordance with this principle, have a length not exceeding about 6 kb, especially not exceeding about 4 kb, in particular not exceeding 3 kb. When the DNA fragment includes the R1 par region A, it will normally have a length not exceeding about 4 kb, especially not exceeding about 2.5 kb, in particular not exceeding about 2 kb. When the DNA fragment comprises the R1 par region B it will normally have a length not exceeding about 2 kb, especially not exceeding about 1.5 kb, in particular not exceeding about 1 kb. It has surprisingly been found that such small, and therefore easily insertable, DNA fragments have retained their stabilizing function, as, by restriction enzyme mapping, the parA region has been narrowed down to a region with a length of about 1800 bp (base pairs), and the parB region has been narrowed down to about 900 bp. It is possible that the gene or genes actually providing a Par+ phenotype are even smaller.

A serious problem in the construction hybrid plasmids with a Par+ phenotype has been the lack of a fast and simple method of screening for this phenotype. In general, the proper hybrid plasmids may be identified by the Par+ phenotype which results in high stability of the plasmid during growth of the plasmid without selection pressure. However, this type of screening is tedious, and in any case it is only relevant if the parent plasmid is unstably inherited. Alternative screening methods have now been developed as outlined below.

(a) Screening for insertion of parA+ fragments

If two different plasmids (from separate incompatibility groups) both carrying the parA+ region are present in the same cell they will dislodge each other with a certain frequency (incompatibility), most likely because they compete for the partition apparatus in the cell. This type of par mediated incompatibility phenotype can be exploited in screening for par hybrids. For instance, a ParA+ plasmid may be transformed to a Δlac *E. coli* strain (e.g. CSH50) harbouring another plasmid carrying the lac genes and the parA+ region. Normally the incoming plasmid will exert par+ mediated incompatibility against the resident ParA+ plasmid. Due to the Lac+ phenotype of the resident plasmid such an incompatibility is easily detected if transformants are selected on the basis of the resistance marker found only on the incoming plasmid, whereas the presence or absence of the resident plasmid is scored on indicator substrates such as McConkey lactose plates. Replica plating colonies from such plates to new similar plates will reveal even low levels of dislodgement of the resident plasmid as colorless colonies showing the occurrence of Lac− cells. A further stability test or a more extensive incompatibility test may be required to test the properties of potential parA+ hybrid plasmids. In this way it is possible—by involving the proper (compatible) combination of incoming and resident plasmids—to quickly screen for insertion of Inc+ (Par+) fragments in any plasmid whether it is unstable or stable.

(b) Screening for insertion of parB+ fragments

Since it also has been demonstrated that two unrelated plasmids which both carry the parB+ region are incompatible with each other the same screening strategy as described for the construction of parA+ hybrids applies to the constructions of parB+ hybrids.

(c) Screening for insertion of ParA+, B+ fragments

Besides having the potential of dislodging both parA+ and parB+ hybrid plasmids according to the descriptions above, the EcoR1-A fragment with the Tn5 insertion allows a direct selection ($Km^R$) for plasmids carrying the parA+, parB+ fragment. Thus, despite the large size of the fragment even very few hybrids are easily selected for. A smaller DNA fragment comprising both par+ regions will of course also exert incompatibility against both parA+ and parB+ plasmids.

DESCRIPTION OF THE DRAWINGS

Reference is made to the drawing in which

FIGS. 1–5 and 7–17 show restriction maps of the plasmids described in the examples.

In FIGS. 1–5 and 7–17, linear restriction maps of the plasmids described in the examples are shown in which the phenotypes and genotypes of the plasmids are indicated above the horizontal line which denotes the parent plasmid. Thus, parA represents one of the regions of plasmid R1 securing plasmid maintenance, parB represents the other region of plasmid R1 securing plasmid maintenance; icel represents a gene mediating immunity to colicin E1; ori or oriV represents the origin of plasmid replication; bla represents a gene encoding resistance to ampicillin; IR represents an inverted repeat structure on Tn5; $Km^R$ represents kanamycin resistance; $Cm^R$ represents chloramphenicol resistance; $Ap^R$ represents ampicillin resistance; $Tc^R$ represents tetracycline resistance; repA represents a gene coding for a protein required for R1 replication; lacZ, lacY and lacA represent the inserted lac operon of which lacZ codes for β-galactosidase, lacY codes for permease and lacA codes for transacetylase; repA-lacZ' represents a fusion between the repA and lacZ genes; copB represents a gene coding for a polypeptide which represses transcription from the repA promoter (of R1 plasmids); copA represents a gene coding for an RNA molecule that inhibits translation of RepA-RNA; $cI_{857}$ represents a gene which codes for a temperature-sensitive λ repressor controlling $\lambda P_R$ promoter activity; Pdeo represents the deo promoter. The arrow denotes the direction of transcription and the "triangles" denote insertions of DNA. The filled-in areas and the blank areas denote inserted genes; the dotted line denotes a deletion. Below the horizontal line, the sites for restriction enzymes are shown in which E denotes EcoR1; P denotes PstI; $B_1$ denotes BamHI except in FIGS. 1 and 5 where, outside the Tn5 DNA, it denotes BalI; $H_1$ denotes HpaI; $E_v$ denotes EcoRV; $B_2$ denotes BglII; $S_1$ denotes SalI; $H_3$ deotes HindIII; and C denotes ClaI.

In FIG. 6, the PstI-D fragment has been mapped further; the numerals above the horizontal line indicate the number of base pairs between the restriction sites. Below the horizontal line, the sites for restriction enzymes are shown in which $R_1$ denotes RsaI; P denotes PstI; and $H_1$ denotes HpaI.

In FIG. 18, stability curves are shown for the $R_1$, p15 and pBR322 derivatives constructed and tested in the examples. Each curve represents the average of at least two liquid cultures followed for more than 100 generations. It appears from the figure that plasmids containing both parA and parB are extremely stably inherited, which is also the case with plasmids containing parB alone and with mini-R1 plasmids stabilized with parA alone.

Figure 4:
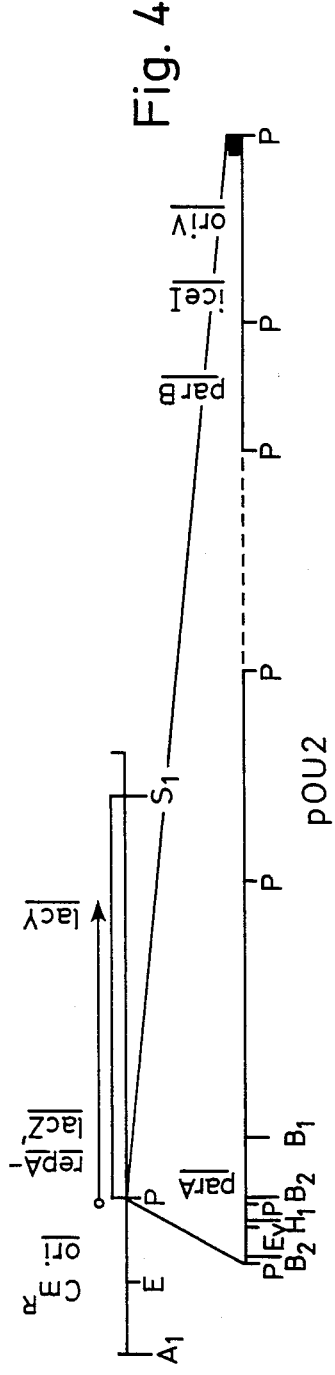

It appears from the curves for Par⁻ plasmids that initially the frequency of plasmid-carrying cells decreases exponentially, as expected, because of a constant rate of loss. At later stages the frequency of plasmid-carrying cells appears to decrease faster (indicated with the full lines) due to a slightly faster growth rate of plasmid-free cells. The dotted line indicates the curve adjusted with respect to this faster growth rate to show the actual frequency of loss.

In contrast, plasmids which are phenotypically Par⁻ are lost with a frequency of $1.5 \times 10^{-2}$/ cell/generation for R1 plasmids, $1 \times 10^{-2}$/cell/ generation for p 15 plasmids and $6 \times 10^{-3}$/cell/generation for some pBR322 plasmids, an example of which is described in Example 3.3. In fact, the loss frequencies of the p15 Par⁻ and pBR322 Par⁻ derivatives are surprisingly high when the copy numbers of these vectors are considered. For example, the copy number of p15 is of the order of 15–20 per cell, predicting a loss rate of $10^{-9}$/cell/ generation if binomial distribution of the plasmids is assumed. Nevertheless, the high loss rate observed is readily explained by the fact that p15 replicons form recA dependent cointegrates, presumably because of the lack of a loxP-like resolution function (Austin et al., Cell 25, 1981, pp. 729–36). Also pBR322 derivatives are known to form cointegrates and when the copy number decreases because of e.g. large cloned fragments, a considerable instability results.

MATERIALS AND METHODS

The strain of *Escherichia coli* K-12 used was CSH50 (Δ pro-lac, rpsL; cf. J. Miller: Experiments in Molecular Genetics, Cold Spring Harbor, New York, 1972). Several plasmids and bacteriophages were used (Table 2).

The experimental techniques used were standard techniques employed in the fields of microbial genetics (J. Miller: Experiments in Molecular Genetics, Cold Spring Harbor, New York, 1972) and genetic manipulation (Davis, Botstein and Roth: A Manual for Genetic Engineering; Advanced Bacterial Genetics, Cold Spring Harbor, New York, 1980).

All cells were grown in LB medium (Bertani, J. Bact 62, 1951, p. 293) with 0.2% of glucose and 1 μg/ml of thiamin, or A+B minimal medium (Clark and Måløe, J. Mol. Biol. 23, 1967, p. 99) supplemented with 0.2% of glucose and 1% casamino acids. The plates used were LA plates containing LB medium and 1.5% of agar.

McConkey lactose indicator plates were prepared as recommended by the manufacturer (Difco), and X-gal plates were prepared by adding 20–40 μg/ml of 5-bromo-4-chloro-indolyl-β-D-galactoside to A+B minimal medium supplemented with 0.2% of glucose and 1 μg/ml of thiamin.

Physico-chemical methods

Clear lysates were prepared according to the method described by Clewell and Helinski, Proc. Natl. Acad. Sci. USA 62, 1969, pp. 1159–66.

Small scale preparation of plasmid DNA was performed by the method of Birnboim et al., Nucl. Acids Res. 7, 1979, pp. 1513–23.

Large scale preparation and analysis of plasmid DNA was performed using dye boyant density gradient centrifugation according to Stougaard and Molin, Anal. Biochem. 118, 1981, p. 181.

Polyacrylamide gel electrophoresis and agarose gel electrophoresis of DNA preparations was carried out essentially as described by Molin and Nordström, Methods in Plasmid Biology, Odense University 1982.

The restriction endonucleases were used in accordance with the prescriptions provided by the manufacturer (Boehringer, Mannheim or Biolabs, New England) at 37° C. Double and triple digests were performed by starting with the enzyme requiring the lowest salt concentration and then adjusting with additional buffer before adding the next enzyme.

Treatment with the exonuclease Bal31 was performed as follows: 0.1 unit of Bal31 was added to 50 μg linear DNA and samples were taken out at 1', 2', 4', 8', 16', 32' and 60' to 60 mM EDTA, extracted with phenol, ethanol precipitated and resuspended in 20 μl TE buffer. Half of the 20 μl was digested with the appropriate restriction enzyme subjected to agarose gel electrophoresis to determine the average size of the deleted DNA deletions. To the other half, the appropriate linker was added and the mixture ligated for 48 hours with an excess of T4 DNA ligase.

Ligation of restricted plasmid DNA was performed as recommended by the manufacturer with the exception of the blunt end ligation, where an excess of T4 DNA ligase and ATP was added.

Microbiological methods

Partitioning test I: The construction of Lac+ vectors made it possible to determine the Par+ phenotype of a plasmid simply by streaking on nonselective McConkey lactose plates or X-Gal plates. Bacteria (Δ lac) harbouring these plasmids mediate a Lac+ phenotype easily scored as colored colonies on the indicator plates, while plasmid-free cells have a Lac− phenotype and appear as colorless colonies.

Partitioning test II: (Used for Lac− plasmids): A colony from a selective plate (a plate containing an antibiotic) was streaked on another selective plate. From this plate, one colony was streaked on an LA plate so as to form single colonies. From the LA plate approximately 10 colonies were suspended in 1 ml of 0.9% of NaCl to a dilution of $10^{-4}$ and $10^{-5}$, respectively. 0.1 ml of the $10^{-4}$ and $10^{-5}$ dilutions were spread on LA plates. From these plates, the resistance pattern of 50 colonies (200 colonies if a weak instability is expected) were tested on the appropriate selective plates. The frequency of loss (LF value) is then calculated on the basis of the formula $$LF = 1 - (v)^{(1/27)}$$

where $v$ is the frequency of plasmid-bearing cells and assuming that one colony grows for 27 generations. Inherent in this method is a large statistical fluctuation.

Partitioning test III: Quantitative measurements of the stability of Lac+ and Lac− plasmids. One complete colony was taken from a selective plate and resuspended in 1 ml of 0.9% of NaCl to a concentration of $10^8$ cells/ml. $2 \times 0.1$ ml of the $10^{-3}$ dilution were used to inoculate $2 \times 10$ ml of LB medium and inoculation was performed at 30° C. with shaking. At a cell density of about $5 \times 10^8$ cells/ml, the cultures were diluted $10^4$ and $10^5$ fold. 0.1 ml of the $10^4$ dilution ($5 \times 10^3$ cells) was used to inoculate 10 ml of fresh LB medium and 0.4 ml of the $10^5$ dilution was spread on McConkey lactose plates, and the plates were inoculated at 30° C. overnight. The dilution from $5 \times 10^8$/ml to $5 \times 10^2$/ml corresponds to 20 generations of growth ($2^{20}$), so the change in the frequency of plasmid bearing cells from one dilution to the next corresponds to that occurring during 20 generations of growth. More generally, the LF value can be calculated as follows:

$$v_1 = (1-LF)^{g_1} \text{ and } v_2 = (1-LF)^{g_2}$$

where $v_1$ and $v_2$ are the frequency of plasmid bearing cells after $g_1$ and $g_2$ generations, respectively and LF is the frequency of loss per cell per generation. Hence, it follows that $$v_1/v_2 = (1-LF)^{g_1-g_2}$$

and $$LF = 1 - (v_1/v_2)^{(1/(g_1-g_2))}$$

Using this formula, errors because of fluctuations in the number of inoculating cells at time zero are avoided. A more convenient approximation of this formula is $$LF = ln(v_1/v_2)/(g_2-g_1)$$

Incompatibility test.

Plasmids believed to carry an inserted par region were screened for by utilizing the observation that two otherwise compatible replicons carrying the same par region are incompatible with one another, leading to the loss of either of the two in the absence of selection pressure. The test is performed by transforming the plasmid to be tested to a bacterial strain carrying another plasmid, selecting for both plasmids on double selective plates. After streaking on a double selective plate (a plate containing two different antibiotics), the incompatibility was measured either qualitatively or quantitatively.

For the qualitative incompatibility test, a colony from the double selective plate was streaked on a LA plate to form single colonies. About 10 colonies from this plate were resuspended in 1 ml of 0.9% NaCl and diluted to $10^{-4}$ and $10^{-5}$, respectively. 0.1 ml of the $10^{-4}$ and $10^{-5}$ dilutions were spread on LA plates. From these plates, 50 colonies (or 200 colonies if a weak incompatibility was expected) were tested on the appropriate selective plates. If a Lac+ plasmid was included in the test, McConkey lactose indicator plates were used instead of replica plating on selective plates. In the case of Lac+ plasmids, the screening was thus performed by transforming suspected Par+ plasmids to a strain already harbouring a Par+ hybrid plasmid mediating a Lac− phenotype. Plasmid incompatibility, and consequently proof of a specific Par+ phenotype of the incoming plasmid is easily detected by screening for Lac− colonies on McConkey plates, showing that the resident Par+ plasmid had been destabilized. An example of this screening procedure is described in Example 4.

Quantitative incompatibility measurements were carried out by measuring the loss frequencies of Lac+ plasmids after establishing heteroplasmid populations as described above. The LF values were measured as described under "Partitioning test III".

Genetic techniques.

Transformation of bacteria was done according to Cohen et al., Proc. Natl. Acad. Sci. USA 62, 1972, pp. 2110–2114, with the modification that when a low transformation frequency was expected, the treatment of the competent cells with DNA on ice was prolonged several hours and after heat shock, the cells were again cooled on ice for 5–30 minutes. This treatment increased the transformation frequency significantly.

Infection with the bacteriophage λ was performed by growing 10 ml cultures overnight in L medium supplemented with 0.2% of maltose (to induce the malB protein which is the λ receptor) with shaking. The cells were washed with 0.9% of NaCl and resuspended in 2 ml 0.01 M MgSo4 and incubated for 1 hour. Dilutions of the λ suspension ($10^0$, $10^{-1}$, $10^{-2}$) were prepared and 0.1 ml of the phage dilution was used to infect 0.2 ml of the suspension of starved cells. The $10^0$, $10^{-1}$ and $10^{-2}$ dilutions of the infection mixtures were spread on selective plates.

To transpose plasmids with Tn5 ($Km^R$) the source of which was the phage λ b221::Tn5, which had been deleted of the attachment site, so that it was unable to lysogenize, a suspension of the phage was used to infect cells harbouring the plasmid onto which transposition was wanted. The infection was performed as described above and kanamycin resistant cells were selected. Several thousand $Km^R$ colonies were collected and 0.1 ml of a $10^{-2}$ dilution of these was used to inoculate 100 ml LB medium. The culture was grown overnight and plasmid DNA prepared from this mixture of cells and used to transform E.coli K12 strain CSH50 to kanamycin resistance.

TABLE 2
Plasmids and Phages

| Plasmids/Phage | Source |
|---|---|
| pKN184 | Nordstrom et al., Plasmid 4, 1980, p. 322. |
| pSF2124 | So et al., Mol. Gen. Genet. 142, 1975, pp. 239–49. |
| pJL99 | Light & Molin, Mol. Gen. Genet. 184, 1981, pp. 56–61. |
| pGA46 | An & Friesen, J. Bact. 140, 1979, pp. 400–407. |
| pKN501 | Molin et al., J. Bact. 138, 1979, pp. 70–79. |
| pF1403-11 | Constructed by inserting the AluI-NaeI fragment from the basic replicon of plasmid of F in the SmaI site of pMC1403 (Casadaban et al., J. Bact. 143, 1980, p. 971), creating a fusion between the E gene of plasmid F and the lacZ gene of pMC1403. |
| pHP34 | Prentki et al., Gene 17, 1982, pp. 189–96. |
| pMC903 | Casadaban et al., J. Bact. 143, 1980, p.971. |
| pKN1562 | Molin et al., J. Bact. 138, 1979, pp. 70–79. |
| pVH1424 | Constructed by P. Valentin-Hansen by inserting a Sau3A fragment carrying the deo promoter from plasmid pVH17 (Valentin-Hansen et al., EMBO J., 1982, 317) in the BamHI site of plasmid pMC1403 (Casadaban et al., op. cit., 971). |
| pSK104 | Constructed by M. Casadaban by inserting a PvuII fragment containing the lac promoter and translation initiation region from pM13mp7 (Messing et al., Nucleic Acids Res. 9, 1981, 309) in the SmaI site of pMC1403, followed by homologus recombination between the lacZ segments. |
| pBR322 | Bolivar et al., Gene 2, 1977, p. 95. |
| pMB1 | Betlach et al., Fed. Proc. 35, 1976, pp. 2037–43. |
| λb221::Tn5 | Berg, D. E., "Insertion and excision of the transposable kanamycin resistance determinant Tn5", in DNA Insertion Elements, Plasmids and Episomes (ed. A. I. Bukhari et al.). |
| EDλ4 | Dempsey and Willetts, J. Bact. 126, 1976, p. 166. |

EXAMPLE 1

Insertion of Tn5 (Km$^R$) in the EcoR1-A fragment from R1

Cells of E.coli K-12 strain CSH50 harbouring plasmid pKN184, a plasmid which consists of plasmid pSF2124 and the 19 kb EcoR1-A fragment (carrying the parA and parB regions) from plasmid R1 (Nordström et al., Plasmid 4, 1980, p. 322), were infected as described under Materials and Methods with a suspension of bacteriophage λb211::Tn5. After selection for kanamycin resistance on LA plates containing 200 μg/ml of kanamycin, colonies were collected and mixed. 0.1 ml of a $10^{-2}$ dilution of these was used to inoculate 100 ml LB medium. The culture was grown overnight, and plasmid DNA prepared from the culture was used to transform E.coli K-12 strain CSH50 selecting for kanamycin resistance on plates containing 200 μg/ml of kanamycin.

In this way, a plasmid, pOU1, was found which mediates resistance to kanamycin and has an insertion of phage DNA corresponding to about 5 kb. (5000 base pairs). The plasmid had a molecular weight/size of 34 kb measured by preparing plasmid DNA and analyzing on agarose gels and the following phenotype: Km$^R$, Ap$^R$, ParA+, ParB+. Plasmid DNA was prepared from pOU1 and the plasmid mapped with restriction enzymes by purifying the plasmid DNA, cleaving it with restriction enzyme(s) and analyzing the resulting fragments by means of agarose gel electrophoresis (cf. FIG. 1). In this way, the λ::Tn5 fragment inserted in the EcoR1-A fragment of pKN184 was identified as carrying the gene coding for Km$^R$, and the location of the fragment was determined as shown in FIG. 1. Plasmid pOU1 was used for further analysis and plasmid constructions.

The strain of E.coli CSH50/pOU1 is deposited in the German Collection of Microorganisms (Deutsche Sammlung von Mikroorganismen, Grisebachstrasse 8, D-3400 Göttingen), in the following abbreviated to DSM, under the Accession No. 2712.

EXAMPLE 2

Construction of a plasmid useful for cloning of par+ fragments

Plasmid pJL99 (Light & Molin, Mol. Gen. Genet. 184, 1981, pp. 56–61) carries a fusion between the repA gene from plasmid R1 and the lac operon; the plasmid mediates a Lac+ phenotype. The PstI-SalI fragment carrying the RepA - lac fusion was excised from pJL99 and inserted in pGA46 which is a p15 replicon (An & Friesen, J. Bact. 140, 1979, pp. 400–407) to construct plasmid, pJL124. A map of the plasmid is shown in FIG. 2. plasmid pJL124 also mediates a Lac+ phenotype on McConkey lactose indicator plates, but it was found that insertion of DNA fragments with little or no promoter activity in the PstI site of pJL124 interferes with the activity of the repA promoter in such a way that these hybrids no longer show up as Lac+ on McConkey lactose indicator plates. However, on the more sensitive X-gal indicator plates, transformant colonies are Lac+ indicating that expression of β-galactosidase is reduced, but not entirely suppressed in the hybrids. Therefore, pJL124 can be used to clone PstI fragments since hybrid plasmids are easily detected on McConkey lactose indicator plates as Lac$^-$ transformants. Moreover, since pJL124 is a p15 replicon and thus unstable, which is easily detected as cells from which the plasmid has been lost form colorless colonies on lactose indicator plates without selection pressure, PstI fragments able to stabilize pJL124 can be screened for on X-gal plates.

The programme for isolating PstI - par+ fragments thus consists of the following steps:

(1) Ligation of pJL124 restricted with PstI and PstI fragments from another plasmid.
(2) Transformation to CSH50 plating on McConkey-lactose plates containing chloramphenicol.
(3) Testing clones that show up as Lac$^-$ on McConkey-lactose plates for stable inheritance of Lac+ phenotype on X-gal indicator plates (cf. Materials and Methods).

The strain E. coli CSH50/pJL124 is deposited in the DSM under the Accession No. 2760.

EXAMPLE 3

Stabilization of unstable plasmids with the parA and parB regions

1. Mini-R1 replicon

Plasmid pOU71, a runaway replication derivative of plasmid pKN1562 which comprises the basic replicon of plasmid R1, the λP$_R$ promoter and cI$_{857}$ repressor gene from phage EDλ4, the gene coding for β-lactamase from the Tn3 transposon and a unique EcoR1 site (a detailed description of the construction of pOU71 is found in Applicant's co-pending application entitled, "Plasmids with Conditional Uncontrolled Replication Behaviour" and filed on the same day as the present application), was restricted with EcoR1, and the EcoR$_1$-A::Tn5 fragment from pOU1 (cf. Example 1) was inserted followed by ligation and transformation of E.coli strain CSH50, selecting of kanamycin resistant cells on LA plates containing 50 μg/ml of kanamycin.

The transformants were screened for the runaway replication phenotype of pOU71 by streaking on LA plates containing 50 μg/ml of kanamycin and incubating at 42° C. Cells containing runaway replication plasmids eventually cease to grow under these conditions. In this way, plasmid pOU71-184 was identified, which had a size of 25.5 kb and the following phenotype: ParA+, Par B+, Ap$^R$, Km$^R$.

The plasmid was mapped with restriction enzymes as described in Example 1 (cf. FIG. 3). From the restriction map it appears that the EcoR1-A::Tn5 fragment has been inserted correctly in the EcoR1 site of pOU71.

Cells harbouring the plasmid were grown on LA plates for 100 generations without selection pressure, i.e. without being grown on plates containing an antibiotic; when determined according to the procedure described in Materials and Methods (Partitioning Test II), the cells were not observed to lose the plasmid, whereas pOU71 was lost from cells grown under similar conditions with a frequency of 1% per generation. Thus, it was determined that pOU71-184 is stably inherited with a frequency of loss of about $10^{-6}$/cell/generation.

The strain of E.coli CSH50/pOU71-184 is deposited in the DSM under the Accession No. 2763.

2. p15 replicon

Plasmid pJL124 (cf. Example 2), which is a Par− p15 replicon, was cleaved with the restriction enzyme PstI and mixed with plasmid pKN184 (cf. Example 1) which had been partially restricted with PstI followed by ligation. The ligation mixed was transformed to E.coli strain CSH50 selecting for chloramphenicol resistance on McConkey lactose indicator plated containing 50 μg/ml of chloramphenicol.

Cells harbouring pJL124 carrying one or more PstI fragments (cf. Example 2) were tested for stable inheritance of the Lac+ phenotype on X-gal plates. One of the stably inherited plasmids was found to contain both the parA and the parB region. This plasmid, pOU2, has a size of 24 kb and the following phenotype: Cm$^R$, Lac+, ParA+, ParB+.

The plasmid was mapped with restriction enzymes as described in Example 1 (cf. FIG. 4). From the restriction map it appears that a PstI fragment has been deleted from the EcoR1-A fragment.

Cells harbouring the plasmid were grown on X-gal plates for 100 generations without selection pressure, and it was determined that pOU2 is stably inherited with an LF-value of less than $10^{-6}$/cell/generation in contrast to pJL124 which was lost from the cells with a frequency of 0.5-1%/cell/generation.

The strain E.coli CSH50/pOU2 is deposited in the DSM under the Accession No. 2713.

3. pMB1 replicon

Plasmid pF1403-11 (cf. Table 2) is an unstably inherited derivative of pBR322 (a pMB1 replicon) carrying a fusion between a gene from plasmid F and the lac operon. The plasmid mediates an Ap$^R$, Lac+ phenotype. The EcoR1-A::Tn5 fragment from plasmid pOU1 (Example 1) was inserted in the unique EcoR1 site of plasmid pF1403-11 immediately upstream of the gene fusion followed by ligation and transformation to E.coli strain CSH50 selecting for Ap$^R$ on plates containing 50 μg/ml ampicillin, Km$^R$ on plates containing 50 μg/ml kanamycin and Lac+ on McConkey lactose indicator plates.

Figure 5:
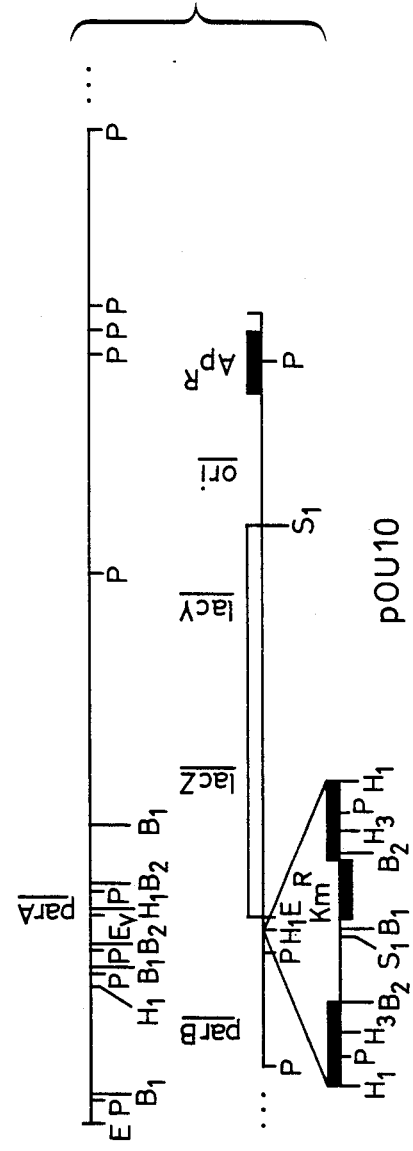

The resulting plasmid pOU10 was mapped with restriction enzymes as described in Example 1 (cf. FIG. 5), and the insertion of the EcoR1-A::Tn5 fragment was verified. The plasmid has a size of 34 kb and the following phenotype: Km$^R$, Ap$^R$, Lac+, ParA+, ParB+.

The plasmid was tested for stable inheritance as described in Example 3.1. Thus, it was demonstrated that pOU10 is stably inherited with an LF-value of less than $10^{-6}$/cell/generation, whereas pF1403-11 was lost from the cells with a frequency of $6 \times 10^{-3}$ per generation.

The strain E.coli CSH50/pOU10 is deposited in the DSM under the Accession No. 2714.

EXAMPLE 4

Cloning of PstI fragments from the EcoR1-A fragment which stabilizes pJL124

The EcoR1-A fragment was restricted with a number of restriction enzymes, and the resulting physical map is shown in FIG. 1. As appears from this figure, the fragment is composed of many PstI fragments. In order to reduce the size of the fragment mediating the Par+ phenotype, it was attempted to subclone par regions possibly carried on one or more of the PstI fragments in the screening vector pJL124 (cf. Example 2). Analysis of a number of clones with the correct phenotype - Lac− on McConkey lactose plates and stable inheritance in the absence of selection pressure - showed that the PstI-D fragment (cf. FIG. 1) mediated this phenotype. No other single PstI fragment was able to stabilize pJL124. The region responsible for stabilization of pJL124 located within the 1.8 kb PstI fragment was denoted parB.

Figure 6:
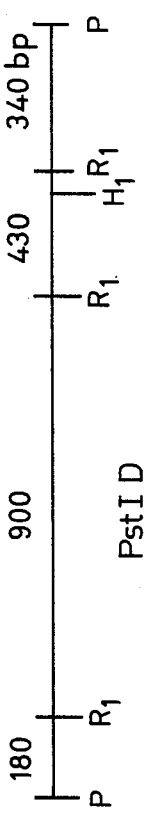
FIG. 6 shows a detailed map (not drawn to scale) of the PstI-D fragment from R1.
Figure 7:
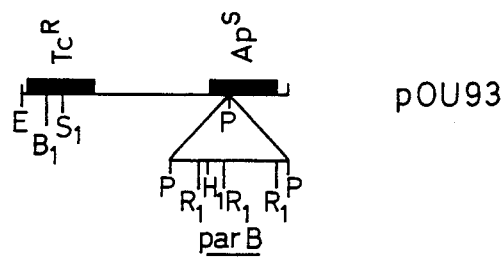
Figure 8:
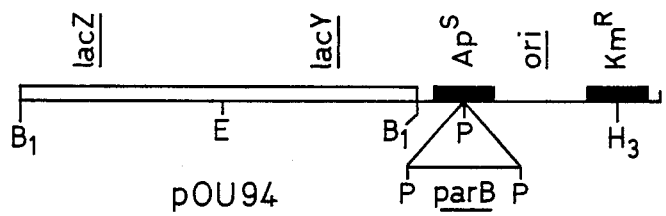

In order to analyse the PstI-D fragment further, the fragment was cloned into the unique PstI site in the bla gene of pBR322 resulting in pOU93 (cf. FIG. 7; the plasmid is deposited in the DSM under the Accession No. 2724). Restriction mapping of this plasmid showed that the PstI-D fragment contains three RsaI sites (cf. FIG. 6). RsaI generates blunt ends, and the 900 bp RsaI fragment was therefore inserted in the SmaI site of plasmid pHP34 (Prentki et al., Gene 17, 1982, pp. 189-96) in the following way. pOU93 was restricted withS RsaI and mixed with pHP34 restricted with SmaI followed by ligation. The ligation mixture was transformed to E.coli strain CSH50 already harbouring plasmid pOU94 (a p15 derivative which is phenotypically Lac+ and ParB+; cf. FIG. 8; the plasmid is deposited in the DSM under the Accession No. 2725), selecting for ampicillin resistance on plates containing 50 μg/ml of ampicillin.

Due to the incompatibility expressed by parB+ regions carried on different plasmids, pOU94 is lost when another plasmid which is phenotypically ParB+ is introduced into the E.coli cells, thus making it possible to select for correct insertions and transformants by streaking the cells onto McConkey plates and screening for colorless colonies (Lac−). One such incompatible plasmid pHP34 derivative which was found to contain the 900 bP RsaI fragment was denoted pOU13. The plasmid has a size of 5.3 kb and the following phenotype: Tc$^R$, Ap$^R$, ParB+.

Figure 9:
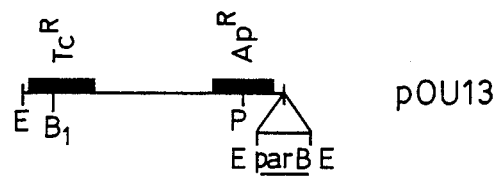

The plasmid was mapped with restriction enzymes as described in Example 1 (cf. FIG. 9). The mapping showed that the RsaI fragment had been converted to a 900 bp EcoR1 fragment as the SmaI site of pHP34 is flanked by two EcoR1 sites.

The strain of E. coli CSH50/pOU13 is deposited in the DSM under the Accession No. 2716.

The 900 bp EcoR1 fragment from pOU13 was inserted in the EcoR1 site of pOU101, an $Ap^R$, $Cm^R$ runaway mini-R1 derivative (a detailed description of the construction of pOU101 is found in Applicant's co-pending application entitled, "Plasmids with Conditional Uncontrolled Replication Behaviour" and filed on the same day as the present application) with a unique EcoR1 site in the cat gene (the gene copending for $Cm^R$), to construct plasmid pOU14 which has a size of 8.2 kb and the following phenotype: $Cm^S$, $Ap^R$, ParB+.

Figure 10:
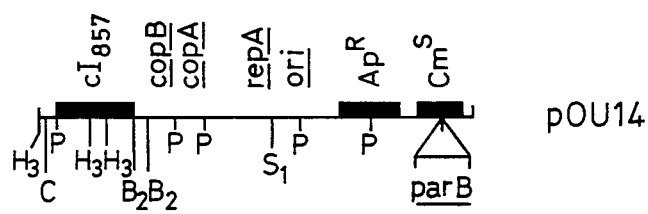

The plasmid was mapped with restriction enzymes as described in Example 1 (cf. FIG. 10).

The plasmid was tested for stable inheritance as described in Example 3.1. Thus, it was demonstrated that, at 30° C., pOU14 is stably inherited with an LF-value of less than $1 \times 10^{-4}$/cell/generation, whereas pOU101 is lost from the cells with a frequency of 1% per generation.

The strain of E. coli CSH50/pOU14 is deposited in the DSM under the Accession No. 2717.

EXAMPLE 5

Stabilization of mini-R1 plasmids with the parB fragment

Figure 11:
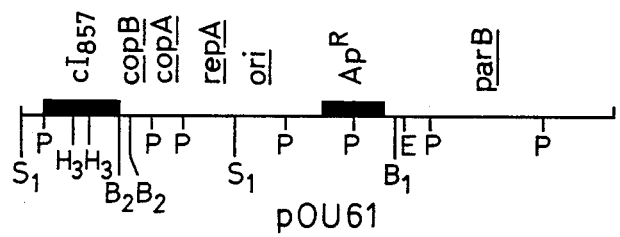

Plasmids pOU90, a runaway replication derivative of pKN1562 which comprises the basic replicon of plasmid R1, the $\lambda P_R$ promoter and $cI_{857}$ repressor from phage ED$\lambda$4, the gene coding for $\beta$-lactamase from the Tn3 transposon and the EcoR1-A fragment from pKN184 (a detailed description of the construction of pOU90 is found in Applicant's copending application entitled: "Plasmids with Conditional Uncontrolled Replication Behaviour" and filed on the same day as the present application), in which derivative the EcoR1-A fragment from pKN184 has been inserted, was restricted with SalI and ligated to produce plasmid pOU61. The plasmid was transformed to E.coli strain CSH50 selecting for a Lac$^-$ phenotype on McConkey plates.

pOU61 was mapped with restriction enzymes as described in Example 1 (cf. FIG. 11). From the restriction map it appears that pOU61 carries the 3.6 kb right end of the EcoR1-A fragment containing the parB region. The plasmid has a size of 10 kb and the following phenotype: ParB+, $Ap^R$, Lac$^-$. The plasmid was tested for stable inheritance as described in Example 3.1. Thus, it was demonstrated that pOU61 is stably inherited with an LF-value of less than $1 \times 10^{-4}$/ cell/generation.

The strain of E. coli CSH50/pOU61 is deposited in the DSM under the Accession No. 2723.

EXAMPLE 6

Stabilization of plasmid pF1403-11 with the parB fragment

Plasmid pOU1 (cf. Example 1) was restricted with SalI and mixed with plasmid pF1403-11 which had also been restricted with SalI followed by ligation and transformation to E. coli strain SCH50, selecting for ampicillin resistant colonies on McConkey lactose indicator plates. Some of these Lac+ clones were screened for stable inheritance of the Lac+ phenotype on McConkey plates as described in Materials and Methods.

Figure 12:
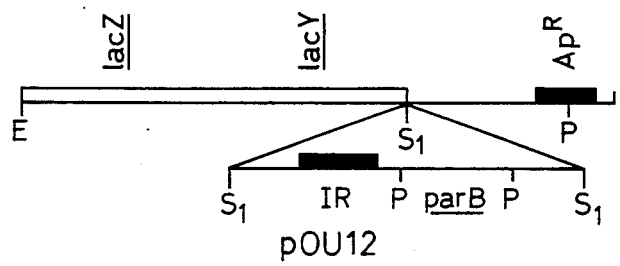

The stably inherited plasmids were mapped with restriction enzymes as described in Example 1 (cf. FIG. 12). From the restriction map it appears that they carry the SalI fragment of pOU1 on which the parB region is located. The plasmid consisting of pF1403-11 ad the SalI fragment from pOU1 was designated pOU12. It had a size of 16 kb and the following phenotype: ParB+, Lac+, $Ap^R$. pOU12 was stably inherited with an LF value of less than $5 \times 10^{-5}$/cell/generation.

The strain of E. coli CSH50/pOU12 is deposited in the DSM under the Accession No. 2715.

EXAMPLE 7

Stabilization of p15 plasmids with the parA fragment

Figure 13:
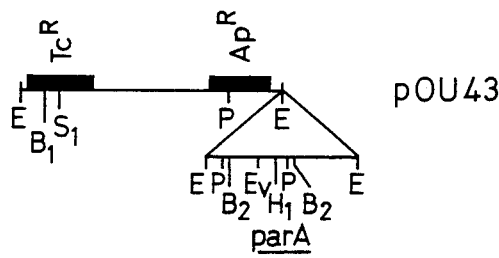

Plasmid pMC 903 (Casadaban et al., J. Bact. 143, 1980, p. 971) was restricted with EcoR1, and the EcoR1 fragment from the plasmid pOU43 (cf. FIG. 13; DSM Accession No. 2720) carrying the parA region was inserted followed by ligation and transformation to E.coli strain CSH50. The resulting plasmid was denoted pOU45 and had a size of 13.4 kb and the following phenotype: ParA+, Lac$^-$, $Ap^R$, $Km^R$.

Figure 14:
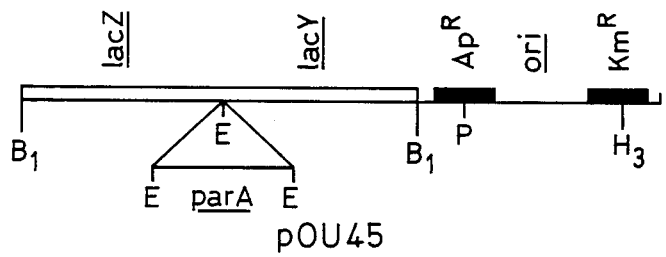

The plasmid was mapped with restriction enzymes as described in Example 1 (cf. FIG. 14). From the restriction map it appears that the parA region has been inserted in the lac operon which is thereby inactivated.

When tested for stability as described in Materials and Methods, the plasmid was found to be stably inherited with an LF value of $8 \times 10^{-4}$/cell/generation, whereas pMC903 has an LF value of 1%/cell/generation.

The strain of E.coli CSH50/pOU45 is deposited in the DSM under the Acc. No. 2721.

EXAMPLE 8

Stabilization of mini-R1 plasmids with the parA region

The EcoR1 fragment from pOU43 was inserted in a mini-R1 plasmid, pOU82, which comprises the basic replicon of plasmid R1, the $\lambda P_R$ promoter and cI repressor gene from phage ED$\lambda$4, the gene coding for $\beta$-lactamase from the Tn3 transposon, the deo promoter and aminoterminal end of the lacZ gene from pVH1424 and the remainder of the lac operon from pSKS104 (a detailed description of the construction of pOU82 is found in the Applicant's copending application entitled "Plasmids with Conditional Uncontrolled Replication Behaviour" and filed on the same day as the present application). Plasmid pOU82 mediates the $Ap^R$ and Lac+ phenotypes and has a unique EcoR1 site useful for cloning EcoR1 fragments. This plasmid is lost with a frequency of 1% per generation in the absence of selection pressure.

Figure 15:
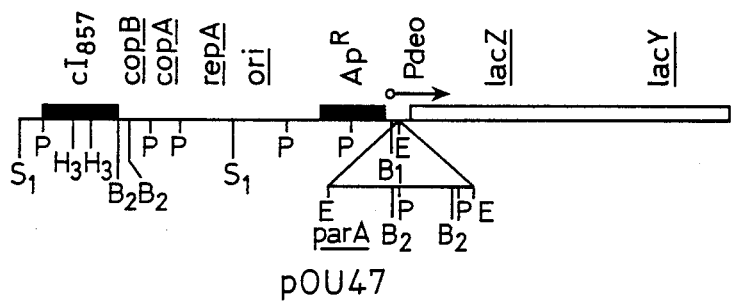

A plasmid in which the 2.4 kb EcoR1 fragment had been inserted in one orientation was denoted pOU47. The plasmid had a size of 14 kb and the following phenotype: ParA+, Lac+, $Ap^R$.

pOU47 was mapped with restriction enzymes as described in Example 1 (cf. FIG. 15).

The strain of E.coli CSH50/pOU47 is deposited in the DSM under Accession No. 2722.

Figure 16:
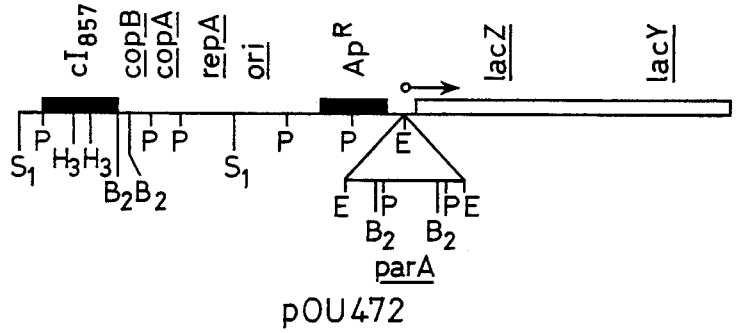

The EcoR1 fragment carrying the parA region was further reduced with 400 bp by means of the exonuclease Bal31; the deletion procedure was performed as described in Materials and Methods utilizing the unique BamHI site of pOU47. The plasmid constructed was denoted pOU472. The plasmid had a size of 13 kb and the following phenotype: ParA+, Lac+, $Ap^R$.

pOU472 was mapped with restriction enzymes as described in Example 1 (cf. FIG. 16). From the restriction map it appears that pOU472 carries the 2.0 kb EcoR1 fragment generated by the Bal31 deletion.

When tested for stability as described in Materials and Methods, the plasmid was found to be stably inherited which means that the entire parA region is contained in the 2.0-kb EcoR1 fragment.

The strain of *E.coli* CSH50/pOU472 is deposited in the DSM under the Accession No. 2726.

EXAMPLE 9

Construction of a mini-R1 plasmid carrying the parA region

Figure 17:
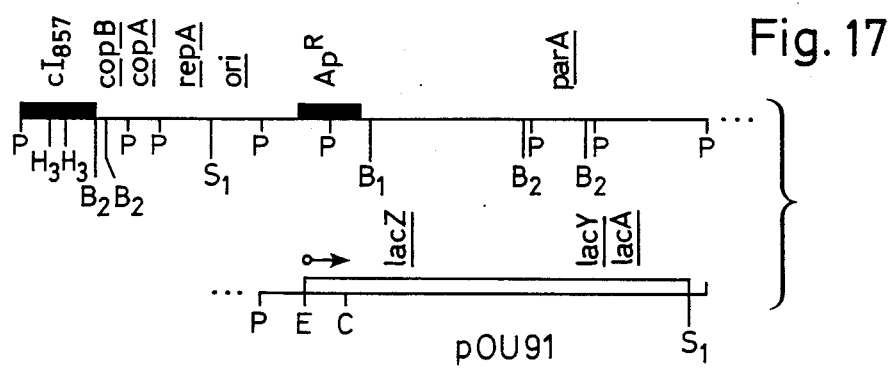
Figure 18:
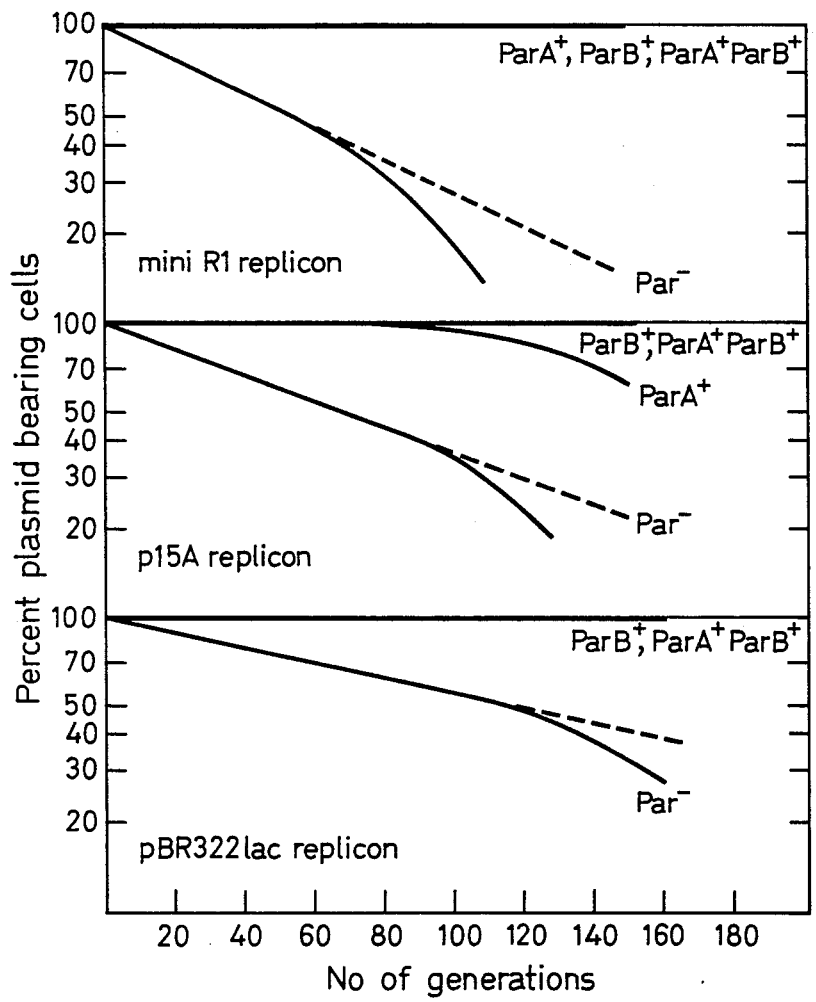
FIG. 18 shows stability curves of different types of replicon carrying different par regions compared to Par− replicons.

Plasmid pOU90 (cf. Example 5) was cleaved with BamHl and partially with Sau3A to delete part of the EcoR1-A fragment, the leftmost 6 kb being retained, followed by ligation. The resulting plasmid, pOU91, was transformed to *E.coli* strain CSH50. pOU91 has a size of 18.75 kb and the following phenotype: Par+, Ap$^R$, Lac+. The plasmid was mapped with restriction enzymes as described in Example 1 (cf. FIG. 17).

Plasmid stability was determined by growing cells containing pOU91 (and, as a control, cells containing pOU82) on McConkey plates without selection pressure at 30° C. for 25 generations; the cells transformed with pOU91 generated red colonies (Lac+), while cells transformed with pOU82 generated both red and white colonies indicating that during the selection-free period, pOU82 had been lost from some of the cells.

The strain of *E.coli* CSH/pOU91 is deposited in the DSM under the Accession No. 2483.

EXAMPLE 10

Construction of a parA+, parB+ mini-R1 plasmid

Plasmid pOU82 (cf. Example 8) is restricted with EcoR1, and the EcoR1 fragment from pOU43 (cf. Example 7 and FIG. 13) carrying the parA region is inserted. This EcoR1 fragment is deleted of the leftmost 500 bp, including one EcoR1 site, by means of the exonuclease Bal31. In the unique EcoR1 site of this plasmid, the EcoR1 fragment from pOU13 (cf. Example 4 and FIG. 9) is inserted. The resulting plasmid, which mediates a ParA+, ParB+ phenotype, may then be transformed to *E. coli* strain CSH50 already carrying plasmid pOU94 and screened for substantially as described in Example 4 with the exception that the pOU82 derivative mediates a weak Lac+ phenotype which means that colonies of cells harbouring this plasmid only will be red in the center and colorless at the edges when grown on McConkey lactose indicator plates.

EXAMPLE 11

Construction of a parA+, parB+ mini-R1 plasmid

Plasmid pOU61 (cf. Example 5) is restricted with EcoR1, and the EcoR1 fragment from pOU43 carrying the parA region is inserted followed by ligation. The resulting plasmid, which mediates a ParA+, ParB+ phenotype, may then be transformed to *E. coli* strain CSH50 which already carries plasmid pOU2 and screened for in a manner corresponding to the procedure described in Example 4. Colonies of cells harbouring the desired plasmid will appear as colorless colonies (Lac−) on McConkey lactose plates. (Throughout the present specification and claims, where par−, Par−, par+ or Par+ is not specifically indicated, the terms par and Par denote the expression of a partitioning function).

We claim:

1. A plasmid which replicates in gram negative bacteria and which has been stabilized by the insertion of a DNA fragment consisting essentially of par region A, par region B or both par region A and par region B of plasmid R1, said DNA fragment having a length under 19 kilobase pairs, the plasmid comprising a gene or genes not naturally related to the plasmid.

2. The plasmid according to claim 1, wherein the inserted DNA fragment comprises both R1 par region A and R1 par region B, said fragment having a length not exceeding about 6 kb.

3. The plasmid according to claim 1, wherein the inserted DNA fragment comprises the R1 par region A, said fragment having a length not exceeding about 4 kb.

4. The plasmid according to claim 1, wherein the inserted DNA fragment comprises the R1 par region B, said fragment having a length not exceeding about 2 kb.

5. The plasmid according to claim 1, further comprising a gene mediating antibiotic resistance.

6. The plasmid according to claim 1, wherein the plasmid is selected from the group consisting of a p15 plasmid or a derivative thereof, and a high copy number broad host range plasmid or a derivative thereof.

7. The plasmid of claim 1, wherein said plasmid is selected from the group consisting of a pMB1 plasmid, a pBR322 plasmid, and derivatives thereof.

8. The plasmid of claim 1, wherein said plasmid has a low copy number during least one stage in the cultivation of bacteria harboring the plasmid.

9. The plasmid of claim 8, wherein said low copy number is about 0.5–5 copies per cell.

10. The plasmid of claim 8, wherein said plasmid is selected from the group consisting of
    (a) plasmids of the incompatibility group IncFII,
    (b) F plasmids,
    (c) low copy number broad host range plasmids, and
    (d) derivatives of plasmids, a, b, or c.

11. The plasmid of claim 8, wherein said plasmid is a conditional runaway replication plasmid.

12. The plasmid of claim 11, wherein said plasmid has a copy number not exceeding about 3–5 copies per cell when host microorganisms containing the plasmid are grown under conditions which insure a low plasmid copy number, and a copy number in the range of at least about 500–1000 copies per cell when the host microorganisms are grown under different conditions insuring a substantially increased plasmid copy number.

13. The plasmid of claim 12, wherein said plasmid has a copy number not exceeding about 3–5 copies per cell at a first temperature at which host microorganisms are grown, and a plasmid copy number in the range of at least about 500–1000 copies per cell at a second higher temperature at which host microorganisms are grown.

14. The plasmid of claim 12, wherein said plasmid copy number is in the range of about 0.5–1 copy per cell under the conditions which insure a low plasmid copy number.

15. The plasmid of claim 12, wherein said plasmid is a plasmid of the incompatibility group IncFII.

16. A bacterium which harbors a plasmid according to claim 1.

17. The bacterium of claim 16 wherein said bacterium is an *Escherichia coli*.

18. A method for producing a gene product of plasmid DNA, comprising cultivating a bacterium harboring the plasmid of claim 1 for production of a gene product, and harvesting said gene product from the bacterial culture.

19. The method of claim 18, wherein the bacterial cultivation proceeds for at least 100 generations of the bacteria.

20. The method of claim 19, wherein the frequency of loss factor of the plasmid from the host cell is less than $2 \times 10^{-4}$/cell/generation.

21. The method according to claim 20, wherein the frequency of loss factor of the plasmid from the host cell is less than $10^{-5}$/cell/generation.

22. The method of claim 21, wherein the frequency of loss factor of the plasmid from the host cell is less than $5 \times 10^{-6}$/cell/generation.

23. A method of screening for the correct insertion of a par region in a plasmid, comprising transforming a bacterium already harboring an unrelated plasmid carrying the same par region as well as mediating a phenotype which is recognizable on appropriate media, with a plasmid believed to carry an inserted par region, culturing said transformed bacterium on said media, and evaluating said culture for the loss of said phenotype as indicative of the correct insertion of the par region.

24. The method according to claim 23, wherein the recognizable phenotype is antibiotic resistance.

25. The method according to claim 23, wherein the recognizable phenotype is Lac+.

26. The method according to claim 23, wherein the par region on said unrelated plasmid is parA.

27. The method according to claim 24, wherein the par region on said unrelated plasmid is parB.

* * * * *

UNITED STATES PATENT AND TRADEMARK OFFICE
CERTIFICATE OF CORRECTION

PATENT NO. : 4,760,022

DATED : July 26, 1988

INVENTOR(S) : Søren Molin and Kenn A. Gerdes

It is certified that error appears in the above-identified patent and that said Letters Patent is hereby corrected as shown below:

```
Front page, second column, first line: "q985"
           should read --1985--.
Abstract,  line 4:    "stablized" should read --stabilized--,
           line 8:    "EcoR1-.A" should read --EcoR1-A--,
           line 15:   "10 31 6" should read --10 -6 --.
Column 1,  line 10:   "factor" should read --factors--,
           line 64:   "formed" should read --termed--.
Column 2,  line 43:   "occuring" should read --occurring--,
           line 49:   "element" should read --elements--,
           line 59:   "or" should read --of--,
           line 66:   "resistace" should read --resistance--.
Column 3,  line 41:   "hose" should read --host--.
Column 4,  line 28:   --a-- should be added after "have".
Column 5,  line 15:   "differing" should read --different--,
           line 59:   "hose" should read --host--.
Column 6,  line 35:   "stabiliztion" should read
                      --stabilization--,
           line 44:   "width" should read --with--,
           line 51:   "generaton" should read --generation--.
Column 8,  line 51:   "DRAWINGS" should read --DRAWING--.
Column 9,  line 28:   "deotes" should read --denotes--,
           line 35:   "R1" should read --R1--,
           line 55:   "p 15" should read --p15--.
Column 10, line 39:   "boyant" should read --buoyant--.
Column 12, line 25:   "Lac-" should read --Lac+--,
           line 49:   "L medium" should read --LB medium--.
Column 13, line 2:    "CSH5O" should read --CSH50--,
           line 24:   "pSK104" should read --pSKS104--,
           line 27:   "homologus" should read --homologous--,
           line 61:   "Plasmid DNA ..." should start a new
                      paragraph.
```

UNITED STATES PATENT AND TRADEMARK OFFICE
CERTIFICATE OF CORRECTION

PATENT NO.  : 4,760,022
DATED       : July 26, 1988
INVENTOR(S) : Søren Molin and Kenn A. Gerdes It is certified that error appears in the above-identified patent and that said Letters Patent is hereby corrected as shown below:

Column 14, line 15: "Iac" should read --Lac--,
           line 17: "Iac" should read --Lac--,
           lines 46-49: "Testing clones..... Methods)." these four lines all belong to (3) and should therefore be indented,
           line 57: --(DSM Accession No. 2471)-- should be added after "pOU71",
           line 67: "EcoR$_1$-A" should read --EcoR1-A--.
Column 15, line 34: "plated" should read --plates--.
Column 16, line 42: "withS" should read --with--,
           line 58: "bP" should read --bp--.
Column 17, line 26: "Plasmids" should read --Plasmid--,
           line 59: "SCH50" should read --CSH50--,
           line 68: "ad" should read --and--.
Column 18, line 12: "from the" should read --from--,
           line 35: --(DSM Accession No. 2482)-- should be added after "pOU82".

Signed and Sealed this

Third Day of April, 1990

Attest:

HARRY F. MANBECK, JR.

*Attesting Officer*      *Commissioner of Patents and Trademarks*